US012788455B2

(12) United States Patent
Zander et al.

(10) Patent No.: US 12,788,455 B2
(45) Date of Patent: Nov. 10, 2026

(54) SYSTEMS AND METHODS FOR ALIGNMENT BETWEEN BONE PLATE AND INTRAMEDULLARY NAIL

(71) Applicant: Stryker European Operations Limited, Carrigtwohill (IE)

(72) Inventors: Nils Zander, Eckernförde (DE); Manfred Wieland, Kiel (DE); Hendrik Kluever, Schoenkirchen (DE)

(73) Assignee: Stryker European Operations Limited, Carrigtwohill (IE)

( * ) Notice: Subject to any disclaimer, the term of this patent is extended or adjusted under 35 U.S.C. 154(b) by 41 days.

(21) Appl. No.: 18/962,599

(22) Filed: Nov. 27, 2024

(65) Prior Publication Data

US 2025/0169861 A1 May 29, 2025

Related U.S. Application Data

(60) Provisional application No. 63/603,813, filed on Nov. 29, 2023.

(51) Int. Cl.
*A61B 17/80* (2006.01)
*A61B 17/17* (2006.01)

(52) U.S. Cl.
CPC ...... *A61B 17/8061* (2013.01); *A61B 17/1728* (2013.01); *A61B 17/8057* (2013.01)

(58) Field of Classification Search
CPC .................. A61B 17/72–7291; A61B 17/1728
See application file for complete search history.

(56) References Cited

U.S. PATENT DOCUMENTS

| | | | | |
|---|---|---|---|---|
| 11,617,606 B2 | 4/2023 | Langdale et al. | | |
| 12,629,193 B2 * | 5/2026 | Korman | ............. | A61B 17/8872 |
| 2007/0219636 A1 * | 9/2007 | Thakkar | ............. | A61B 17/1721 623/18.11 |
| 2015/0105779 A1 * | 4/2015 | Smith | ................ | A61B 17/1725 606/71 |
| 2017/0333102 A1 * | 11/2017 | Peterson | ............ | A61B 17/1717 |
| 2019/0000509 A1 * | 1/2019 | Cowens | ............. | A61B 17/1728 |
| 2024/0156499 A1 * | 5/2024 | Zander | ............... | A61B 17/8061 |
| 2025/0090207 A1 * | 3/2025 | Machamer | ......... | A61B 17/1725 |

* cited by examiner

*Primary Examiner* — Matthew J Lawson
(74) *Attorney, Agent, or Firm* — Lerner David LLP

(57) ABSTRACT

A method of attaching a fixation construct to a long bone includes attaching a guide block to a bone plate, placing the bone plate against a surface of the long bone, connecting two k-wires to the guide block, locating the medial-lateral direction, confirming an overlapping alignment of the two k-wires in the medial-lateral direction, confirming a positioning of the bone plate with respect to the bone, and securing the bone plate to the bone.

19 Claims, 9 Drawing Sheets

SYSTEMS AND METHODS FOR ALIGNMENT BETWEEN BONE PLATE AND INTRAMEDULLARY NAIL

CROSS-REFERENCE TO RELATED APPLICATION

The present application claims priority to U.S. Application No. 63/603,813 filed Nov. 29, 2023, the disclosure of which is incorporated herein by reference.

BACKGROUND OF THE INVENTION

The present disclosure generally relates to a fracture fixation system and a surgical method for implanting the same, and more particularly, to a fracture fixation system including a bone plate, an intramedullary rod, and fasteners.

Femoral fractures are often treated with fixation devices and systems, such as a bone plate and intramedullary nail combination system. These systems affix fractured bone portions together and provide stability to the bone during osteogenesis. For the insertion of such systems, a surgeon first inserts a nail into the medullary canal of a patient's long bone. Once the nail is secured in place, the bone plate is placed against the bone such that the holes within the bone plate align with the holes of the intramedullary nail. Fasteners are then driven through the bone plate and the nail to provide additional fixation to the fracture to reset comminuted areas of the fractured bone.

Traditional methods of inserting fracture fixation systems are not without drawbacks. Because the intramedullary nail is inserted before the bone plate, the final position of the bone plate is determined from the initial position of the nail. Accordingly, bone plates may be prevented from placement at optimal areas of the fractured outer cortical bone for the sake of aligning with the underlying nail. Such a sub-optimal alignment may result in a longer recovery time for a patient and further associated complications.

Thus, improvements in fracture fixation methods are desired.

BRIEF SUMMARY OF THE INVENTION

According to one aspect of the present disclosure, a method of attaching a fixation construct to a long bone includes: inserting a first portion of a reference body into a medullary canal of the long bone; attaching an alignment flange to a second portion of the reference body extending outside of the bone; placing a bone plate into a location against a surface of the long bone; aligning the bone plate with the alignment flange; and securing the bone plate to the bone.

In another aspect, the step of aligning the bone plate includes aligning a handle removably secured to the bone plate with the alignment flange.

In a different aspect, the step of aligning the bone plate further includes aligning a marker on the handle with a marker on the alignment flange to place the bone plate at a corresponding linear location on the surface of the long bone along a longitudinal axis of the reference body.

In a further aspect, the step of aligning the bone plate further includes aligning the handle against a surface of the alignment flange to place the bone plate at a corresponding angular location on the surface of the long bone about a longitudinal axis of the reference body.

In another aspect, the step of placing includes the location being on a lateral surface of the long bone.

In a different aspect, the method further includes removing the reference body and the alignment flange.

In another aspect, before the step of aligning the bone plate with the alignment flange, the step of placing the bone plate is initially influenced by contours of the surface of the long bone.

In a further aspect, the step of securing the bone plate includes inserting a fastener through an aperture of the bone plate and into the long bone.

In another aspect, the method further includes inserting an intramedullary nail into the medullary canal of the long bone after the reference body has been removed from the long bone.

In a different aspect, the step of inserting the intramedullary nail includes aligning a targeting arm attached to a proximal end of the nail with a portion of the secured bone plate.

In another aspect, the method further includes inserting a fastener through both an aperture of the bone plate and an aperture in the intramedullary nail.

In yet another aspect, the step of inserting the first portion of the reference body includes expanding an exterior portion of the reference body into an interference fit within the bone to anchor the first portion of the reference body at least partially within the bone.

In a further aspect, the step of inserting the first portion of the reference body includes threading a portion of the reference body into the bone.

In a different aspect, the step of inserting includes inserting the reference body into the bone to a depth at which an indent of the reference body is flush with an outer cortex of the bone.

In another aspect, the method further includes manipulating the alignment flange to align a first marker on a first end of the alignment flange with a second marker on a second end of the alignment flange in a medial-lateral direction of the long bone;

In a different aspect, the method further includes aligning condyles of the long bone under fluoroscopy to locate the medial-lateral direction.

In another aspect, the method further includes rotationally holding the alignment flange to the reference body after the first and second markers are aligned.

In yet another aspect, the method further includes rotating the reference body and alignment flange as a single construct after the alignment flange is rotationally locked to the reference body.

In a different aspect, the method further includes inserting a k-wire through an opening of the alignment flange.

According to another aspect of the present disclosure, a method of attaching a fixation construct to a long bone includes: inserting a first portion of a reference body into a medullary canal of a long bone; attaching an alignment flange to a second portion of the reference body extending outside of the bone; manipulating the alignment flange such that a first marker disposed on a distal end of the alignment flange is aligned with a second marker disposed on a proximal end of the alignment flange in a medial-lateral direction of the long bone; placing a bone plate against a lateral surface of the bone such that a handle extending from the bone plate contacts the alignment flange and a marker on a handle extending from the bone plate aligns with at least one of the first and second markers on the alignment flange; and securing the bone plate to the bone.

In another aspect, the method further includes, before the step of placing the bone plate, rotationally securing the alignment flange to the reference body.

In a different aspect, the method further includes removing the reference body and the alignment flange from the bone.

In another aspect, the method further includes inserting an intramedullary nail into the medullary canal such that a hole axis of the bone plate aligns with a hole axis of the intramedullary nail.

In a different aspect, the method further includes inserting a fastener through a hole of the bone plate and through a hole of the intramedullary nail.

In another aspect, the method further includes rotationally locking the alignment flange to the reference body by engaging a locking mechanism of the alignment flange to contact the reference body.

In a different aspect, the step of securing the bone plate includes driving at least one bone screw through a hole of the bone plate into the bone.

According to another aspect of the present disclosure, an implant alignment system includes: a reference body extending along a longitudinal axis including a first portion configured to be embedded within a long bone and a second portion configured to extend outside of the bone; and an alignment flange rotatably and removably couplable to the second portion of the reference body, the alignment flange including an extension arm extending substantially transverse to the longitudinal axis when the alignment flange is coupled to the reference body, the extension arm having a first marker, a base having a second marker, and a detent configured to rotatably secure the alignment flange to the reference body.

In another aspect, the system further includes a handle configured to removably attach to a bone plate.

In a different aspect, the alignment flange includes a third marker corresponding to a nail depth, the third marker configured to align with an indicator disposed on the handle.

In a further aspect, the alignment flange includes a fourth marker corresponding to a rotational position of the alignment flange relative to the reference body.

In yet another aspect, the reference body further includes a neck portion with a reduced diameter between the first and second portions.

In a further aspect, the detent includes a spring-loaded lever.

In yet another aspect, the system further includes a bone plate.

In a different aspect, the bone plate further includes a guide block mountable to the bone plate.

According to another aspect of the present disclosure, a method of attaching a fixation construct to a long bone includes attaching a guide block to a bone plate; placing the bone plate against a surface of the long bone; connecting two k-wires to the guide block; locating the medial-lateral direction; confirming an overlapping alignment of the two k-wires in the medial-lateral direction; confirming a positioning of the bone plate with respect to the bone; and securing the bone plate to the bone.

In another aspect, the step of attaching may include aligning holes in the guide block with holes in the bone plate. The step of attaching may further include securing the guide block to the bone plate by inserting a fixation screw through one of the holes in the guide block and into one of the holes in the bone plate.

In a further aspect, the step of attaching may include removably securing a handle to the guide block. The step of placing the bone plate may include manipulating the handle to place the bone plate on a lateral surface of the long bone.

In a different aspect, the step of placing the bone plate may initially be influenced by contours of the surface of the long bone.

In another aspect, the step of connecting the two k-wires may include inserting an end of each of the k-wires into the guide plate such that the k-wires extend anteriorly from the guide plate. The step of connecting the two k-wires may further include the k-wires being non-parallel. The step of connecting the two k-wires may include the k-wires extending along diverging axes. The step of connecting the two k-wires may include the k-wires being disposed within a plane that is substantially parallel to the transverse plane. The step of connecting the two k-wires may include inserting the ends of each of the k-wires at a location on the guide block at a distal end of the bone plate placed against the surface of the long bone.

The step of locating may include aligning condyles of the long bone under fluoroscopy. The step of confirming the positioning of the bone plate with respect to the bone may include aligning the overlapping k-wires with a surface of the intercondylar fossa of the femur to confirm the positioning of the bone plate along a proximal-distal axis of the femur. The method may further include inserting a guide wire at an entry point of the distal end of the long bone and into the long bone parallel to a medullary canal thereof, and the step of confirming the positioning of the bone plate with respect to the bone may include aligning the bone plate with the guide wire to confirm the positioning of the bone plate along an anterior-posterior axis of the femur.

In a further aspect, the step of securing the bone plate may include inserting a fastener through a hole of the bone plate and into the long bone.

In a different aspect, the method may further include inserting an intramedullary nail into the medullary canal of the long bone. The step of inserting the intramedullary nail may include aligning a targeting arm attached to a proximal end of the nail with a portion of the secured bone plate. The method may further include inserting a fastener through both a hole of the bone plate and a hole in the intramedullary nail. The step of inserting the intramedullary nail may include inserting the intramedullary nail such that a hole axis of the bone plate aligns with a hole axis of the intramedullary nail.

BRIEF DESCRIPTION OF THE DRAWINGS

The features, aspects, and advantages of the present invention will become better understood with regard to the following description, appended claims, and accompanying drawings in which:

DETAILED DESCRIPTION OF THE PREFERRED EMBODIMENTS

Figure 1:
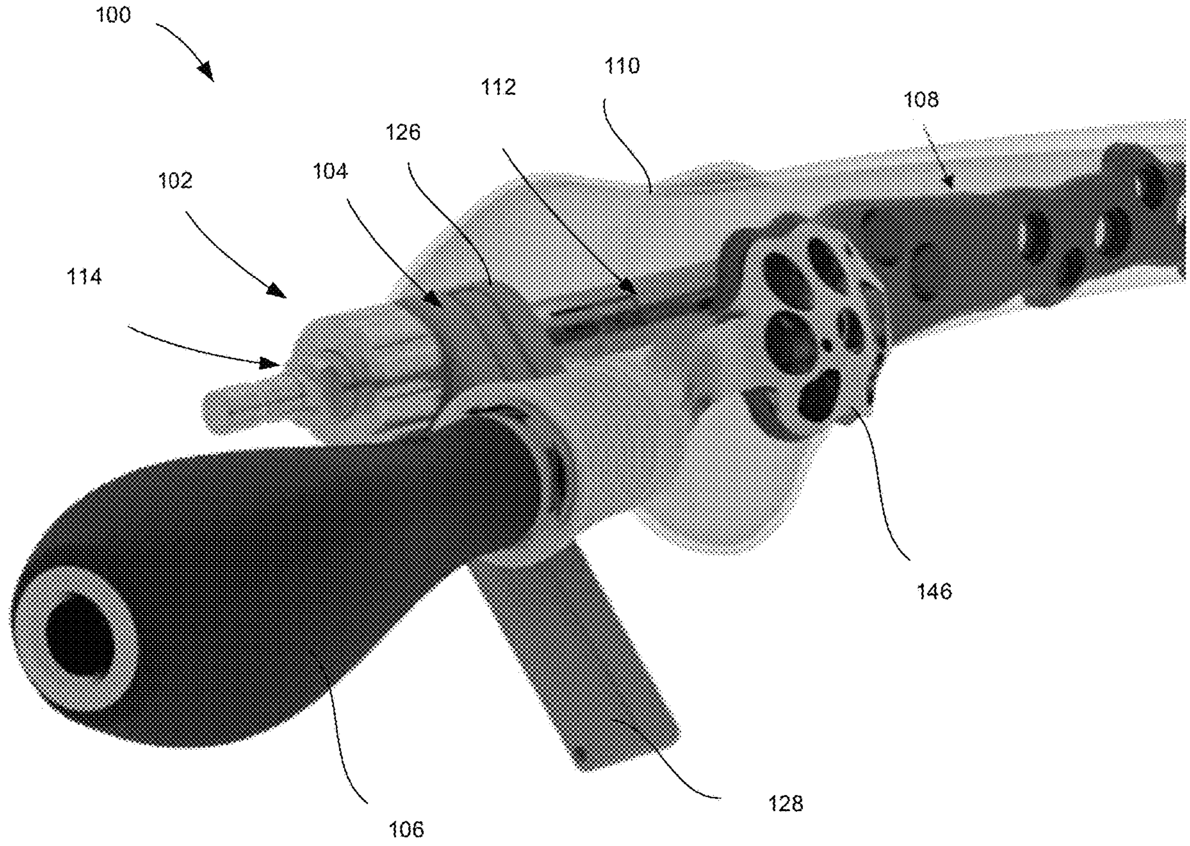
FIG. 1 is a perspective view of various insertion instruments for a fracture fixation system according to one embodiment.

Reference will now be made in detail to the various embodiments of the present disclosure illustrated in the accompanying drawings. Wherever possible, the same or like reference numbers will be used throughout the drawings to refer to the same or like features within a different series of numbers (e.g., 100-series, 200-series, etc.). It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

In describing certain aspects of the inventions disclosed herein, specific terminology will be used for the sake of clarity. However, the inventions are not intended to be limited to any specific terms used herein, and it is to be understood that each specific term includes all technical equivalents, which operate in a similar manner to accomplish a similar purpose. In the drawings and in the description which follows, when referring to the term "proximal" in the context of the bone, the term "proximal" refers to the end of the component that is closer to the heart, while the term "distal" refers to the end of the component that is further from the heart. In the drawings and in the description which follows, when referring to the term "proximal" refers to the end of the instrumentation, or portion thereof, which is closest to the operator in use, while the term "distal" refers to the end of the instrumentation, or portion thereof, which is farthest from the operator in use.

FIG. 1 illustrates a fracture fixation insertion system 100 used for implant alignment that is implemented with a patient's femur according to one embodiment of the present disclosure. Insertion system 100 includes a reference body 102, an alignment flange 104 attachable to reference body 102, and a handle 106 contacting the alignment flange 104 and extending from a guide block or a strut or plate inserter 146 that is connected with a bone plate or strut 108. Although the embodiments described herein and illustrated in the figures depict an insertion system 100 used in conjunction with a patient's femur, it is appreciated that insertion system 100 may be implemented with other bones, particularly long bones such as the tibia, humerus, and the like.

Figure 2:
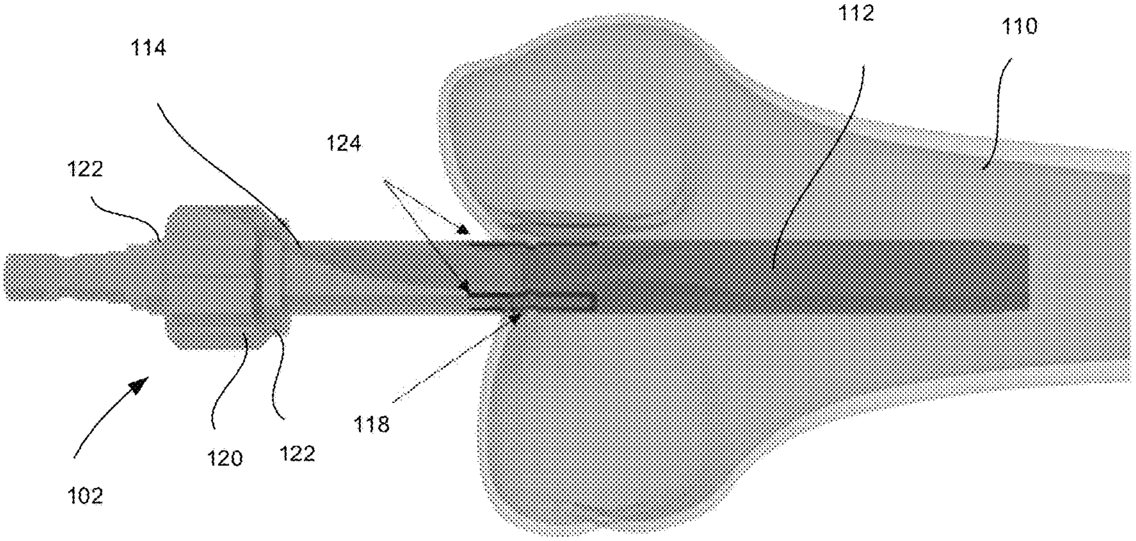
FIG. 2 is a side view of a reference body of the fracture fixation system of FIG. 1 inserted into a long bone.

FIG. 2 illustrates a side view of reference body 102 partially inserted into a femur 110. Reference body 102 is tubular and extends along a longitudinal axis. A first end or distal end 112 may be tapered or otherwise narrowed to aid in insertion of reference body 102 into femur 110. Reference body 102 is preferably hollow to allow drill bits, drivers, or other instruments to be inserted within a central cannula of reference body 102. Proximal of the tapered distal end 112, reference body 102 has a substantially uniform diameter that that is smaller than the distance defined between two condyles 116 of femur 110 to allow reference body 102 to be inserted within a medullary canal of femur 110. An indent or neck 118 is defined between the distal end 112 and a proximal end 114 of reference body 102. Neck 118 has a reduced diameter and acts as a signal or visual indicator to an operator that reference body 102 has been properly seated within femur 110 when neck 118 is posited at or near the edge or outer surface of the cortical bone.

Continuing with the embodiment of FIG. 2, second end or proximal end 114 of reference body 102 extends proximally from neck 118 and includes a diameter substantially similar to or equal to the diameter of distal end 112. Proximal end 114 includes a knob 120 extending circumferentially around proximal end 114. Knob 120 is knurled or otherwise textured to aid an operator in gripping the knob in use. Various steps or shoulders 122 may be formed on either the proximal or distal side of knob 120 to act as physical stops for knob 120. Reference body 102 includes at least one finger 124 along an exterior portion of reference body 102 configured to extend outward upon actuation to engage the femur 110 to secure reference body 102 in place relative to the bone. This can for example be a component of reference body 102 or any other component passed through the inside of the tubular structure of body 102 to push fingers 124 outward from the inside. Fingers 124 are generally formed by cuts or slits in the central portion of body 102 to create a cantilever structure. An internal component on fingers 124, such as that created at neck 118, can be a structure by which fingers 124 are forced outward when pushed from the inside of body 102. In other words, body 102 may have a smallest inner diameter at neck 118 by way of an annular ridge on body 102, including on fingers 124. Once another component or element of body 102 is inserted into body 102 to contact the annular ridge, the corresponding portions of body 102 including fingers 124 can be flexed outward, even slightly, which can create an interference fit at the local bone site. In some embodiments, a spring or other biasing member may be positioned within reference body 102 or at an exterior connection between reference body 102 and finger 124 to force finger 124 radially outward away from the longitudinal axis of the reference body 102.

Figure 3:
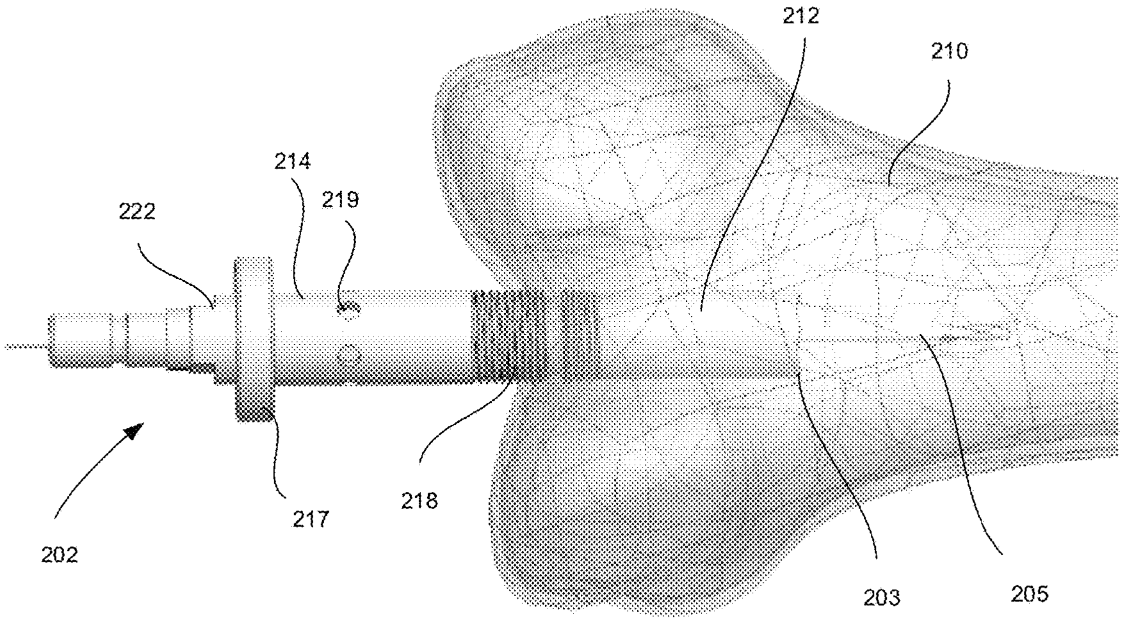
FIG. 3 is side view of another embodiment of a reference body inserted into a long bone.

FIG. 3 illustrates a reference body 202 according to another embodiment of the present disclosure. In this embodiment, reference body 202 is similar to reference body 102, and therefore like elements are referred to with similar numerals within the 200-series of numbers. Reference body 202 acts as a Trephine design reference body and is configured to remove a circular cross-section portion of bone as it is inserted. As such, reference body 202 is substantially hollow and includes teeth 203 at a distal end 212 configured to cut into bone 210. A drill bit 205 is insertable down a central cannula of reference body 202 to create a pilot hole within bone.

Continuing with the embodiment of FIG. 3, reference body 202 extends from a distal end 212 to a proximal end 214 and includes a threaded portion 218 therebetween. Threaded portion 218 allows the reference body to be screwed into the bone to secure reference body 202 in place. Similar to neck 118, threaded portion 218 defines a distinct neck, which can be a break in the threaded section, that can act as a depth gauge to a user to indicate to a user when the reference body 202 is seated at an ideal location when the threaded portion 218 aligns with a cortical region of bone.

Proximal end 214 of reference body 202 is tubular with a similar or equal diameter to distal end 212. Proximal end 214 includes a circular flange 217 extending radially outward from reference body 202 and acts as a gripping portion for a user and acts as a seat for an alignment flange to be positioned against. The proximal end 214 and circular flange 217 may also be attached to an external tool, such as a driver, to aid in insertion of reference body 202. Various steps or shoulders 222 may be formed on the proximal side of flange 217. Proximal end 214 further includes a plurality of apertures 219 spaced around the circumference of proximal end 214 to aid in the securement of an alignment flange to reference body 202 in discrete rotational positions. Apertures 219 may also aid in the extraction of gas and bone fragments as the reference body 202 is drilled into the bone. Such an alignment flange may attach to reference body 202 by extending pegs or nodes of the alignment flange through or at least partially into apertures 219, or by other attachment methods. Apertures 219 can also be present in reference body 102 at the same location and for the same purpose.

FIGS. 1 and 4-11 illustrate a monolithic alignment flange 104 according to one embodiment of the present disclosure in various stages of implantation of an implant system. Alignment flange 104 includes an attachment portion 126 and an extension arm 128 extending away from the attachment portion 126. Attachment portion 126 includes a central opening configured to receive a portion of the reference body 102. As such, the diameter of the central opening may correspond to the diameter of reference body 102.

Attachment portion 126 includes a holding mechanism, such as detent 130, positioned within an exterior surface of attachment portion 126. Detent 130 is configured to secure both the rotational and axial position of alignment flange 104 relative to reference body 102. Detent 130 operates as a cantilever or a spring-loaded lever and is extendable between a locked and an unlocked configuration. In the locked configuration, a node on the interior surface of detent 130 extends at least partially into one of the plurality of apertures spaced around the circumference of proximal end 114 of reference body 102 to temporarily rotationally fix alignment flange 104 in a specific position with respect to reference body 102. In the unlocked configuration illustrated in FIGS. 6-7, detent 130 slides around an outer surface of attachment portion 126. As such, detent 130 may bias inward toward reference body 102 in both the locked and unlocked configurations.

Extension arm 128 extends outward from attachment portion 126 in a direction perpendicular or substantially perpendicular to the longitudinal axis of reference body 102. Extension arm 128 is planar and defines a uniform thickness across its length. A plurality of markers are defined on and/or within both extension arm 128 and attachment portion 126 that can be viewed under fluoroscopy to aid an operator in aligning a bone plate 108 with reference body 102. The rest of the material of alignment flange 104 is radiolucent so the markers can stand out visually when under fluoroscopy.

First and second markers 132, 134 are positioned within a lateral side 140 of alignment flange 104. First and second markers 132, 134 may be indicia printed onto the alignment flange or metal components embedded within the alignment flange material and visible by X-ray, or holes or divots formed within the alignment flange, or the like. First and second markers 132, 134 assist an operator with frontal plane alignment. As such, as viewed from the medial or lateral side, (1) with both condyles 116 aligned one over the other, and (2) when first marker 132 and second marker 134 aligned, reference body 102 is considered to be in an optimal rotational position such that for securing reference body 102 to the bone via finger(s) 124. Third marker 136 extends along the length of extension arm 128 at the midpoint of extension arm 128. Thus, third marker 136 may be a line printed onto extension arm 128 that is visible by X-ray, a groove formed within extension arm 128, or the like. Third marker 136 is configured to align with a marker of a handle 106 (see FIG. 10) to indicate an optimal depth of reference body 102 to a user.

Figure 11:
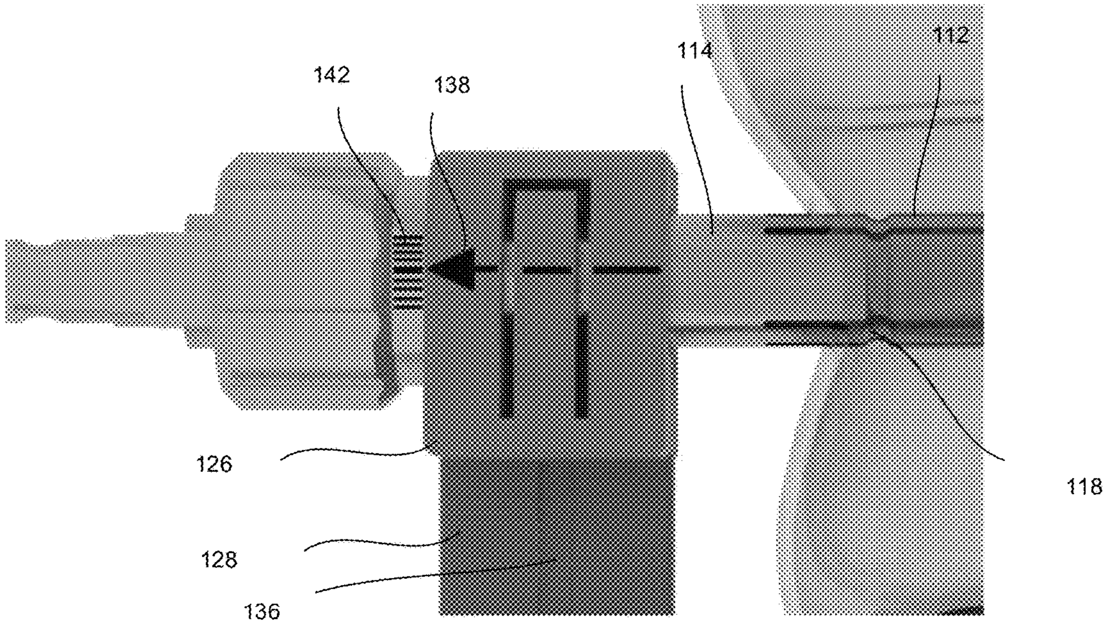
FIG. 11 is a side view of a portion of the insertion instruments of FIG. 1.

FIG. 11 illustrates a fourth marker 138 positioned on attachment portion 126 of alignment flange 104. Fourth marker 138 may be a radiopaque printing onto alignment flange 104, a groove formed within alignment flange 104, or the like. Fourth marker 138 may align with an indicator 142 on reference body 102 to indicate or ensure the proper rotational position of alignment flange 104 relative to reference body 102. In turn, an operator may lock alignment flange 104 to reference body 102 once an optimal rotational position of alignment flange 104 is realized. This can be done by a set screw or the like.

Figure 7:
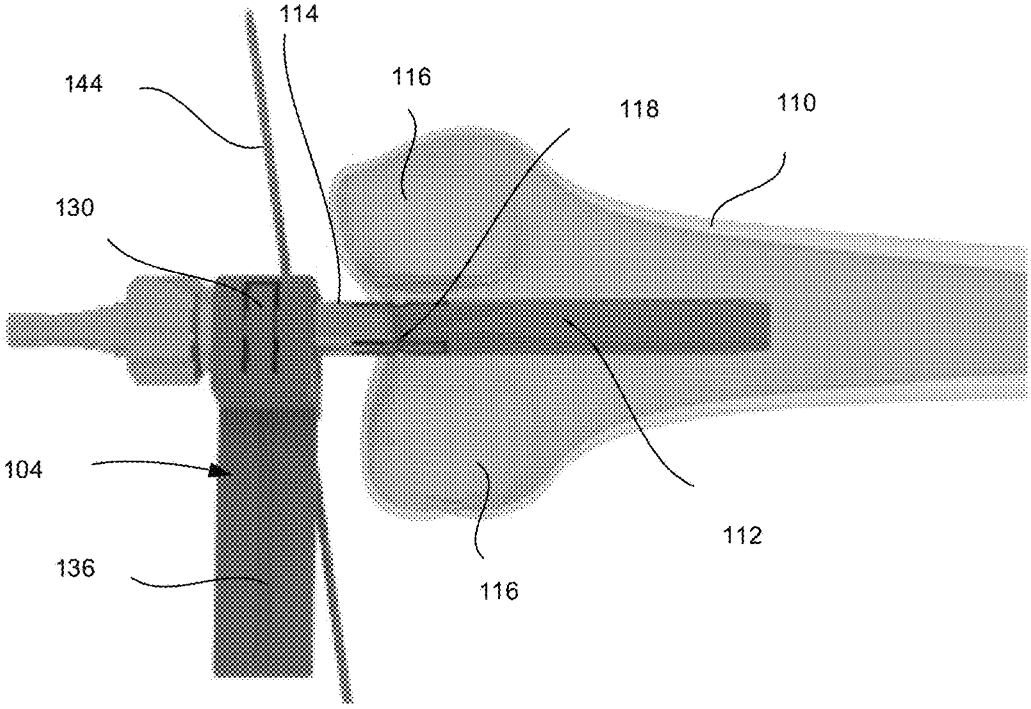
FIG. 7 is a side view of the reference body and alignment flange of FIG. 4 with an additional k-wire.

FIG. 7 illustrates a k-wire 144 implemented with alignment flange 104 to check the lateral distal femur angle. Alignment flange 104 includes at least one opening for receiving k-wire 144. Once k-wire 144 is inserted through this opening, the angle of the k-wire 144 relative to the alignment flange 104 and femur 110 may be measured to ensure a proper lateral distal femur angle is achieved. In some examples, an optimal lateral distal femur angle is between 70° and 90°, more preferably 81°.

FIGS. 8-11 illustrate a guide block or strut inserter 146 according to one embodiment of the present disclosure. Guide block 146 is generally elongate and includes a head portion 148 at one end and a handle portion 150 at an opposite end. Head portion 148 includes a plurality of holes 152 configured to align with a corresponding plurality of holes in a head portion of a bone plate 108. As such, the plurality of holes 152 are arranged in a pattern that corresponds with the same pattern of holes in the head portion of the bone plate 108. Head portion 148 may further include one or more locator pins positioned on an underside of the head portion 148 to help position head portion 148 against bone plate 108, such that the locator pins fit into dedicated and similarly sized recesses in bone plate 108. Guide block 146 may include additional holes for receiving sutures, k-wires, or the like therethrough.

Handle portion 150 extends from head portion 148. Handle portion 150 may define a rectangular, circular, or other cross-sectional shape. A proximal end 151 of handle portion 150 may include various attachment features to allow a handle 106 (illustrated in FIG. 1) to attach thereto. Such attachment features may include threads, friction fits, snap fits, quick connect mechanisms, and the like. Handle portion 150 includes a curved portion 154 along its length that allows the handle portion 150 to extend away from the underlying bone and contact alignment flange 102 in use.

Figure 10:
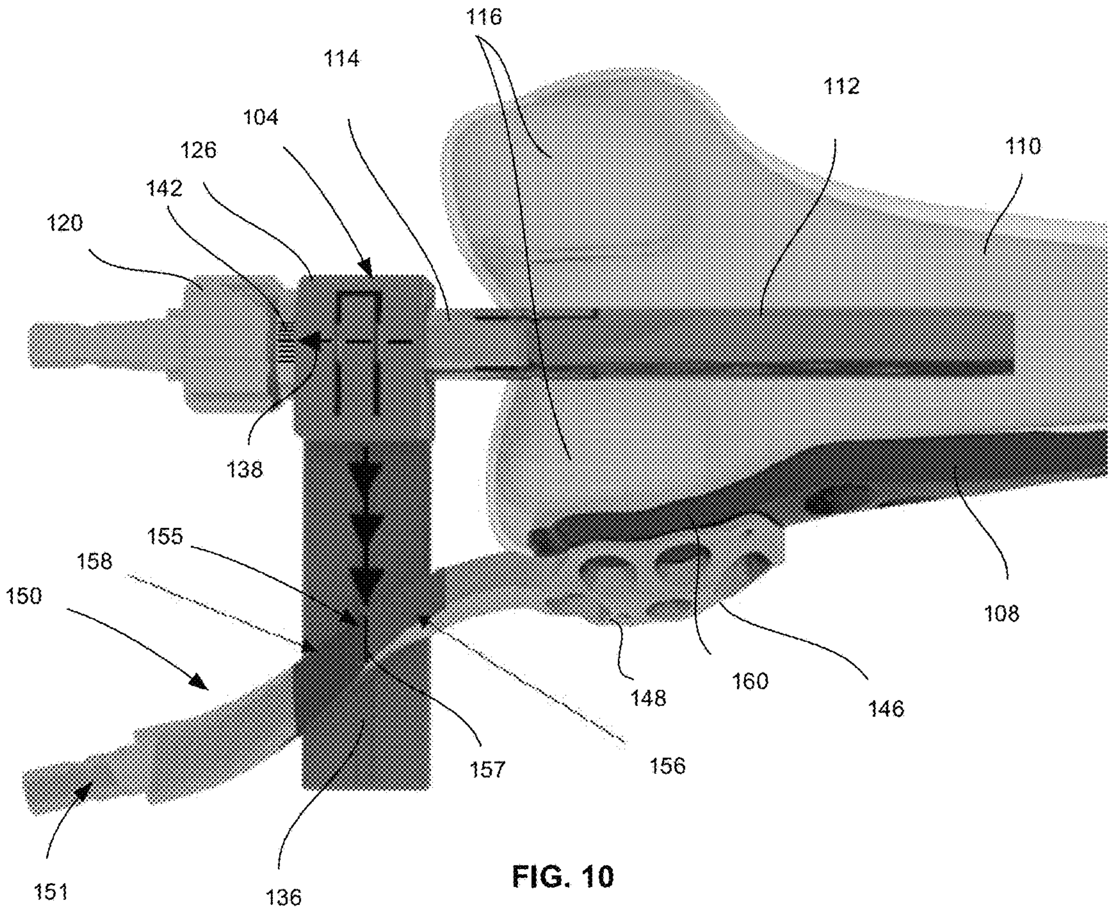
FIG. 10 is a side view of the insertion instruments for inserting the fracture fixation system of FIG. 8.

FIG. 10 illustrates a nail depth indicator 155 disposed on handle portion 150. Nail depth indicator 155 includes a central indicator 157 configured to align with third marker 136 disposed on alignment flange 104. Nail depth indicator 155 further includes first and second regions 156, 158 that indicate whether a reference body 102 will be positioned at a proper depth within femur 110.

Figure 8:
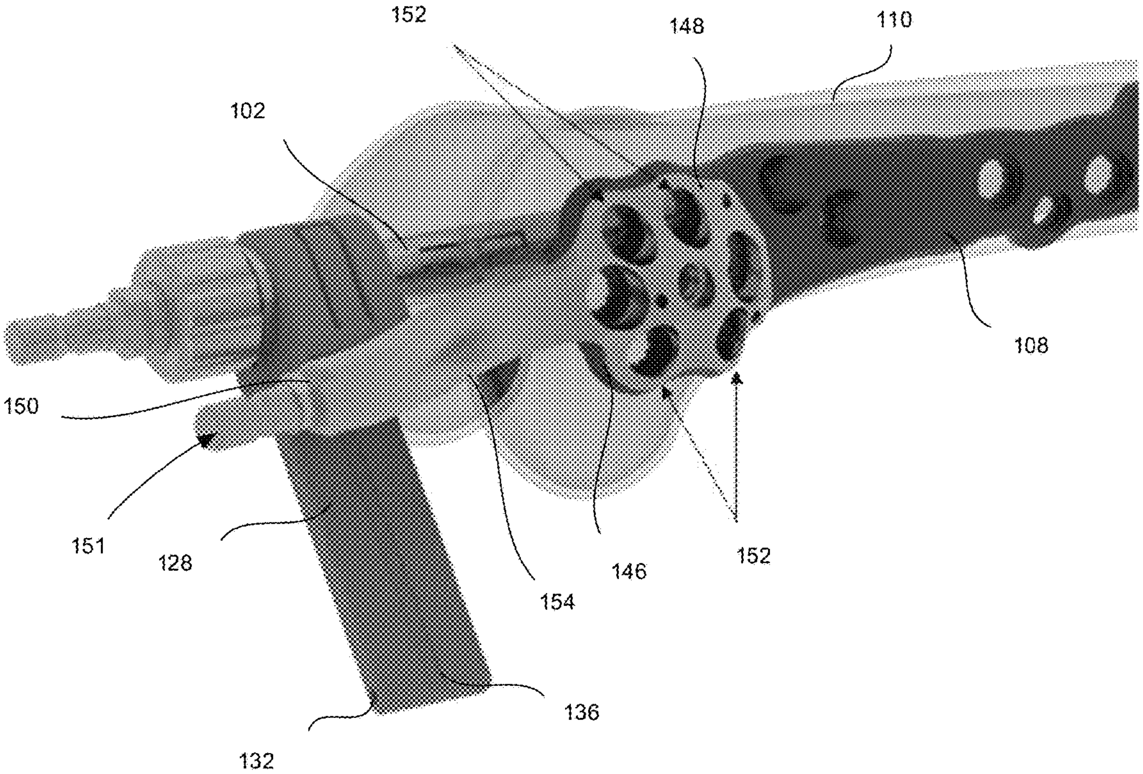
FIG. 8 is a perspective view of the insertion instruments for inserting the fracture fixation system of FIG. 1.
Figure 9:
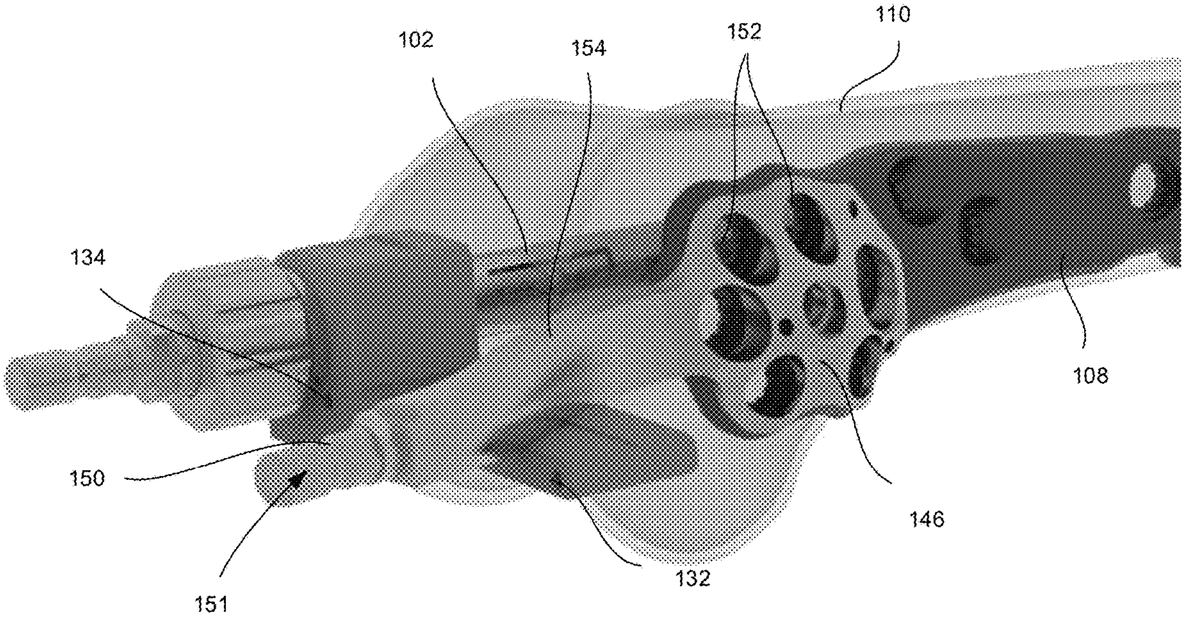
FIG. 9 is another perspective view of the insertion instruments for inserting the fracture fixation system of FIG. 8.

FIGS. 8-10 illustrate a bone plate or strut 108 according to one embodiment of the present disclosure. Bone plate 108 is depicted as a femoral bone plate designed for lateral placement against the bone, but it is appreciated that other bone plates configured and contoured for placement on exterior surfaces of long bones may be implemented with system 100. Other bones with which bone plate 108 may be used are the tibia, humerus, etc. Bone plate 108 includes a head portion 160 defined at a first end and a tail portion extending away from the head portion. Head portion 160 includes a plurality of holes shown beneath holes 152 of head portion 148 of guide block 146 and arranged in a pattern that causes bone screws driven through such holes to extend into femur 110 and, for some, into various corresponding holes of an intramedullary nail. Head portion 160 may further include locator holes for locating alignment pins disposed on guide block 146, as discussed above. It is appreciated that bone plate 108 may be an optimally-selected bone plate for a particular fracture, and that a particular bone plate may be selected before an intramedullary nail is selected.

A method of implementing insertion system 100 which aids in attaching a fixation construct to a long bone is provided herein. An operator first assesses the patient's fracture and, with the knee in flexion, creates access to the fracture by removing tissue surrounding the bone. This can occur using a lateral parapatellar approach to the distal lateral femur. Once access to the distal end of the femur is created, the operator may identify an entry point for a reference body. Such an entry point may be created in the medullary canal of the bone through the intercondylar notch. Once the entry point is identified, a k-wire is inserted into the medullary canal. Radiographic confirmation can ensure proper location. An entry portal can be created at the entry point using a reamer sleeve with a handle, and a trocar assembly over the k-wire.

Reference body 102 may be inserted into the entry portal by inserting the tapered first portion 112 of reference body 102 into the entry portal and into the medullary canal of the bone. First portion 112 may be inserted to a depth in which indent 118 aligns with an outer surface of cortical bone. This can be done with or without the k-wire, which if used is removed after reference body 102 is placed in the bone. Once the depth is set, an operator may provisionally anchor reference body 102 to the bone by extending fingers 124 outward to engage femur 110 and secure reference body 102 in place. Such a depth may be adjusted or readjusted at a later point of time based on the markings of an alignment flange 104.

Alternatively, reference body 202 may be inserted into a medullary canal of femur 110 without the creation of an entry portal, and either with or without the prior insertion of the k-wire. A drill bit 205 may be positioned through a central cannula of reference body 202 and be used to drill a pilot hole into femur 110. Reference body 202 may then be centered around the pilot hole and is then rotated to allow teeth at a distal end of reference body to cut into the bone and remove a cylindrical plug of bone. Reference body 202 may be inserted to a depth in which a threaded portion 218 or a neck therein aligns with an outer surface of cortical bone. Such a depth may be adjusted or readjusted at a later point of time based on markings of an alignment flange 104.

Figure 4:
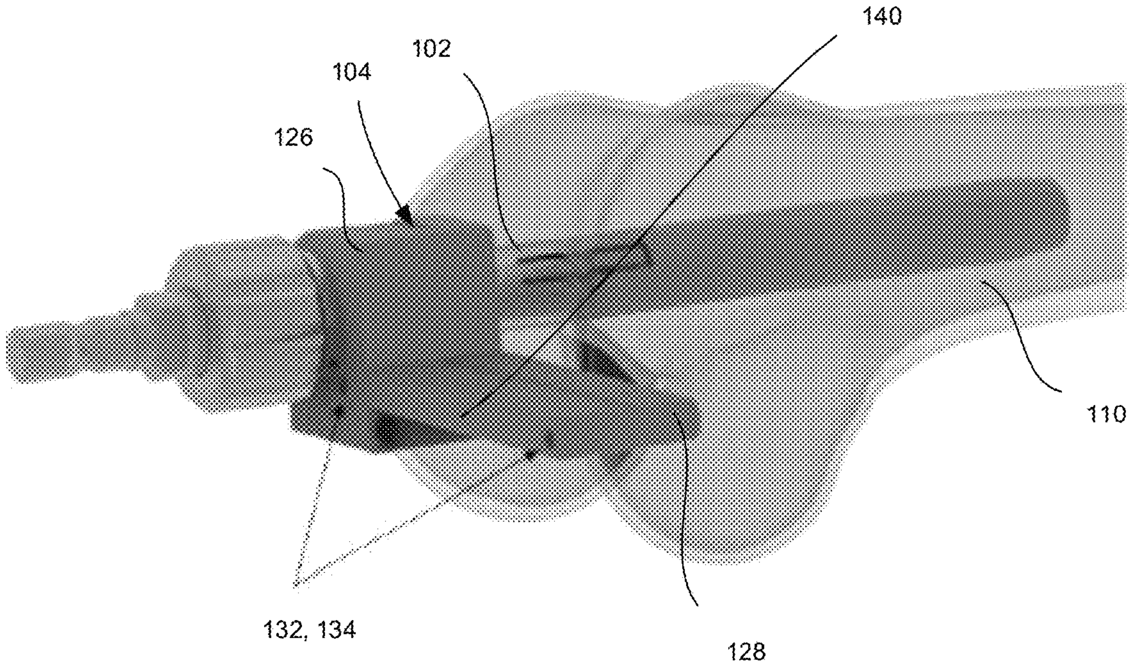
FIG. 4 is a perspective view of a reference body and alignment flange of the fracture fixation system of FIG. 1.
Figure 5:
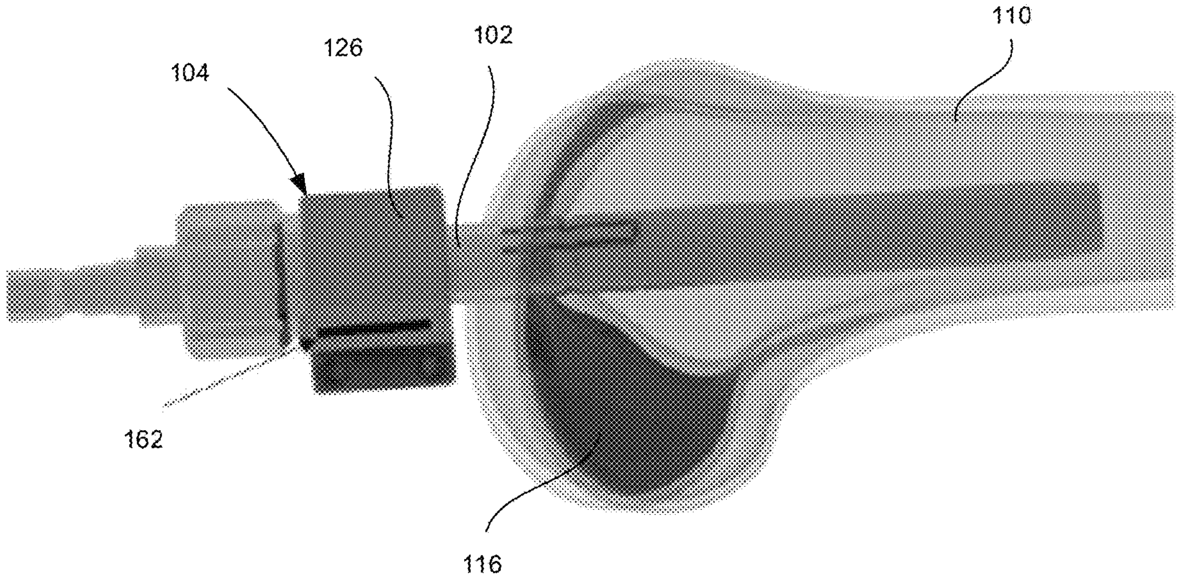
FIG. 5 is a side view of the reference body and alignment flange of FIG. 4.
Figure 6:
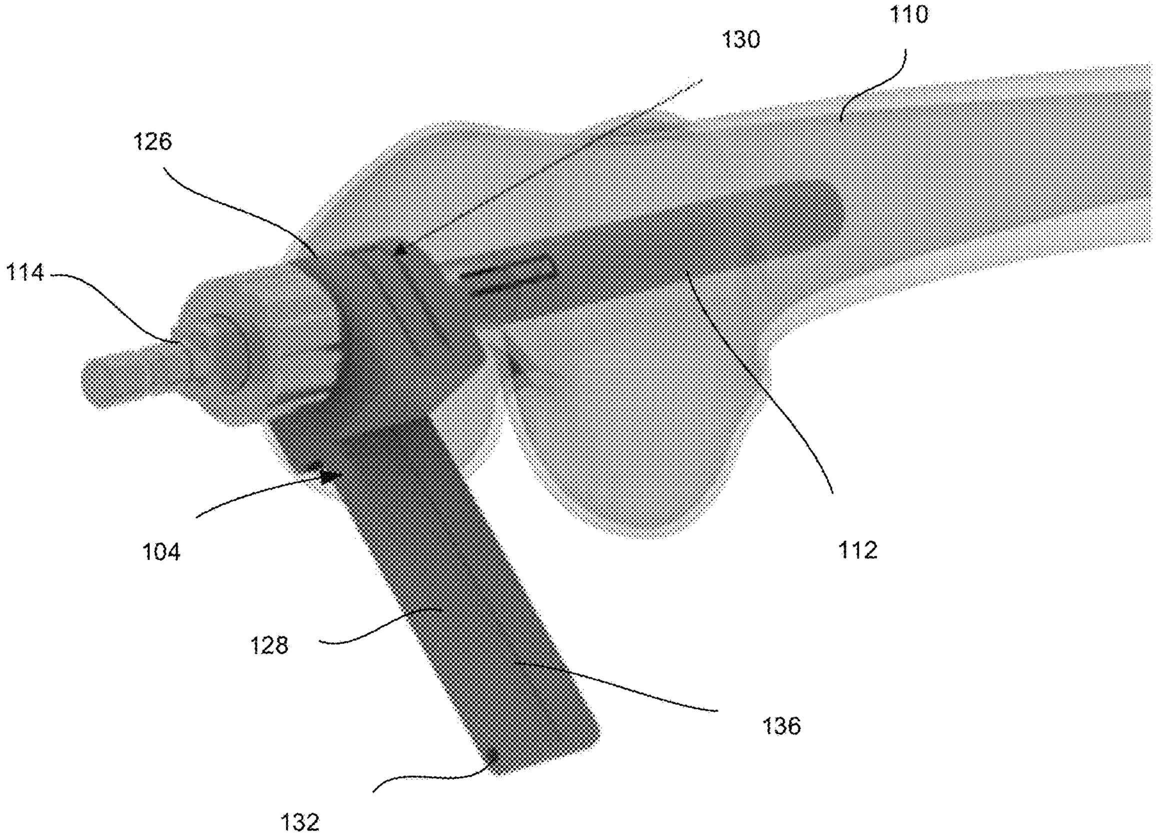
FIG. 6 is another perspective view of the reference body and alignment flange of FIG. 4.

Alignment flange 104 is preinstalled onto a second portion of reference body 102 or 202 that extends outside of femur 110 before insertion. In other embodiments, alignment flange 104 may be clipped or otherwise attached over reference body 102 or 202 after reference body 102 or 202 is inserted. Alignment flange 104 is attached to reference body 102 by rotationally locking the alignment flange 104 to reference body 102 by pressing a detent 130 disposed within attachment portion 126 to engage the underlying reference body, as depicted in FIGS. 4-5. Then, an operator may assess first and second markers 132, 134 disposed on alignment flange 104 with X-ray or other imaging technology to ensure alignment of the frontal plane of femur 110. Alignment flange 104 may be rotated about reference body 102 such that first and second markers 132, 134 align and form a continuous line 162, such as the continuous line depicted in FIG. 5. This continuous line is visualized in a sagittal plane perpendicular to a medial-lateral direction and is also shown against a visual alignment of the condyles. Once a continuous line 162 is realized, an operator may lock the reference body to the bone by further extending fingers 124 outward (if not already fully secured) to engage femur 110 and secure reference body 102 in place. Before such locking steps occur, an operator may optionally insert a k-wire 144 through an opening of alignment flange 104 to further assess the lateral distal femur angle, and various adjustments to reference body 102 may be made to ensure an optimal lateral distal femur angle is realized. Such a k-wire insertion is illustrated in FIG. 7.

A bone plate 108 may then be placed against a lateral surface of femur 110. To avoid prematurely contacting alignment flange 104, alignment flange 104 may be rotationally released from reference body 102 and rotated such that extension arm 128 extends away from the lateral surface of femur 110. Bone plate 108 may then be positioned in a medically optimal location against the bone that best secures the underlying fracture. This positioning takes into account the anatomical landmarks of the lateral surface at the distal end of femur 110 to identify the best anatomical fit for the contoured inner surface of bone plate 108 to sit against the contoured exterior surface of femur 110. In some instances, only anatomical landmarks and no extra tools or guides are used to guide the surgeon's placement of plate 108 by hand. To aid in manipulating bone plate 108 during positioning, guide block 146 and handle 106 may be secured together and may be attached to the head portion 148 of bone plate 108 prior to placement of bone plate 108 against the bone. Handle 106 may be removed after initial insertion of bone plate 108 and while its final position is determined prior to securing bone plate 108. The bone plate 108 may be preliminarily fixed to the femur 110 by inserting k-wires through holes of the bone plate into the underlying bone. The k-wires may also help with the reduction of the fragments of femur 110.

Once bone plate 108 is in a medically optimal position, if not removed already, handle 106 may be removed from guide block 146 to allow an operator more room to visualize the handle portion 150 of guide block 146. Alignment flange 104 may then be rotated toward its previous position so that it clicks into place and an upper side of extension arm 128 contacts handle portion 150. This clicking into place as or prior to extension arm 128 contacting handle portion 150 is done by the node on the interior surface of detent 130 extending across the plurality of apertures spaced around the circumference of proximal end 114 of reference body 102, and helps to ensure that a proper lateral position of bone plate 108 is achieved. If alignment flange 104 cannot be placed in its initially identified orientation because it is either short of contacting handle portion 150 or else because it reaches handle portion 150 before coming to its initially identified orientation with respect to reference body 102, reference body 102 can be unsecured from femur 110 and readjusted, or else the location of bone plate 108 can be readjusted so that the alignment of reference body 102 and bone plate 108 are in sync.

An operator may now assess the third and fourth markers 136, 138 disposed on alignment flange 104 to ensure the nail depth and angular orientation of an intramedullary nail will be properly positioned relative to the anchored bone plate 108. This is done by placing handle portion 150 on the top surface of attachment portion 126 of alignment flange 104 (if not already so positioned). A line between first and second regions 156, 158 on alignment flange 104 is visually aligned with third marker 136 on extension arm 128 to properly set the linear location on the bone surface and therefore the depth of the intramedullary nail to be placed within femur 110. In one embodiment, second region 158 can be colored red, so that alignment of an arrow of third marker 136 indicates a protruding nail if the intention is to interlock the nail with bone plate 108. Similarly, first region 156 can be colored green which would indicate a nail sunk too far into the bone if attempting to interlock the nail with bone plate 108.

During alignment, either plate 108 or reference body 102 can be relocated as necessary to achieve a location for both elements that achieves proper alignment. Since alignment flange 104 is temporarily fixed to a particular axial location along reference body 102, and since neck 118 of reference body 102 is located at the edge of the bone surface, proper alignment of the central indicator 157 between first and second regions 156, 158 on alignment flange 104 ensures a position of the intramedullary nail at a specific location tied to the initial and provisional placement of plate 108 so that the later implanted nail will not protrude from the bone.

Proper rotational information is also gathered from aligning fourth marker 138 on attachment portion 126 with indicator 142 on reference body 102. Later placement of the nail will tolerate a certain degree of misaligned rotation before any oblique locking screws could interfere with the femoral-patellar joint. Information about rotation of the plate and the resulting orientation of the nail when the two are interlocked is helpful to ensure an optimal placement.

After each of the markers of alignment flange 104 have been aligned and bone plate 108 is preliminarily secured to femur 110, insertion system 100 may be removed from femur 110 by detaching the spreading mechanism of the reference body from the bone, and removing the reference body/alignment flange construct from the bone. Bone plate 108 can be secured to femur 110 using locking screws. In other embodiments, locking screws can be used to fix bone plate 108 before reference body 102 is removed, since the locking screws are angled to miss the intramedullary nail to be implanted.

Figure 12:
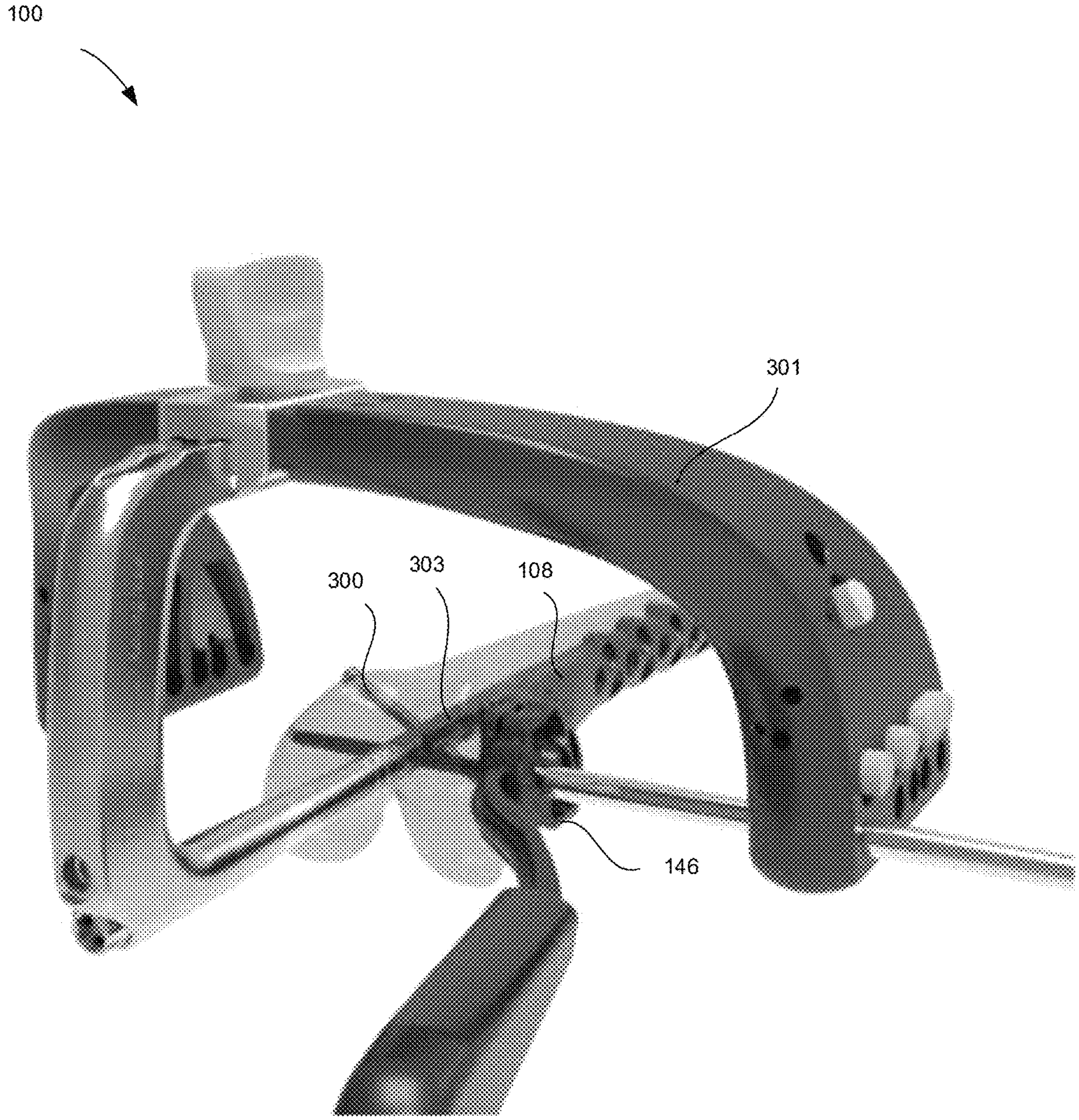
FIG. 12 is a perspective view of various targeting instruments used in conjunction with the fracture fixation system of FIG. 1.

After insertion system 100 is removed from the femur 110, an operator may insert an intramedullary nail 303 into the medullary canal of the femur 110, as is illustrated in FIG. 12. This is done by connecting a drill guide such as guide block 146 to the anchored plate 108, and using an alignment or targeting arm 301 attached to the end of intramedullary nail 303. The targeting arm 301 and/or any cannula attached to it can be aligned in a specific way to guide block 146 and/or the anchored plate 108, thus allowing the intramedullary nail 303 to be seated in its proper intended location using plate 108 as a reference. In other words, targeting arm 301 and/or any cannula are aligned with the features of the implanted plate 108 so that the position of the nail 303 is set to the implanted plate 108. Targeting arm 301 can be rotated and maneuvered as needed to fit the attached nail 303 is the proper location as to its depth and rotation. After linking is performed, additional rotational and axial fixation of nail 303 to bone 110 can be performed using targeting arm 301. Then proximal locking of nail 303 is carried out.

Because the alignment of reference body 102 was measured relative to bone plate 108, axes of the holes of bone plate 108 align with axes of holes of an intramedullary nail that is designed for use with the particular bone plate 108. As such, additional fasteners, such as bone screw 300 may be driven through bone plate 108 and through an intramedullary nail 303, for example by using the attached targeting arm 301 and guide block 146, to secure plate 108 to the nail and to fix the fracture. The ultimate length of the nail is not dependent upon the foregoing insertion method, since the proximal end of the nail is used as a reference while seating the bone plate 108.

Another method of implanting a bone plate 108 does not include all components of system 100. Such method begins with preparation of the bone site and insertion of the k-wire 314 at the entry point on the distal femur and into the femur parallel to its medullary canal, as described above. However, neither reference body 102 nor 202 is utilized in this alternative method.

Figure 13:
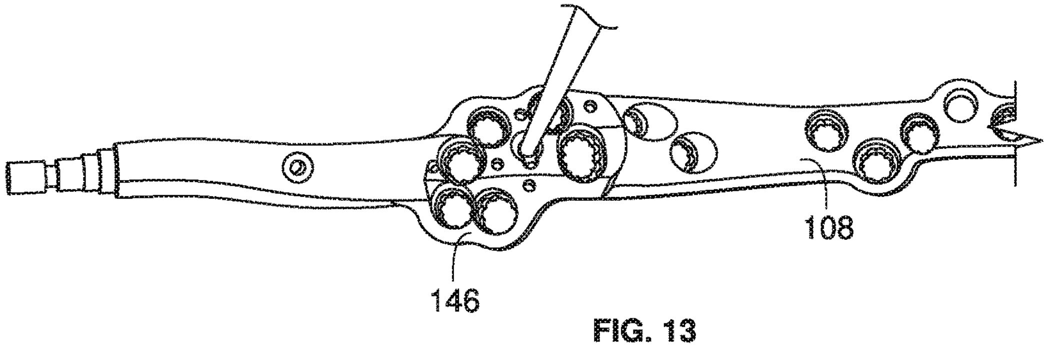
FIG. 13 is a perspective view of an insertion instrument secured to a bone plate according to another embodiment.

Guide block 146 is placed on bone plate 108 and secured as discussed above. This can include inserting a fixation screw through a central hole in guide block 146 and into a corresponding hole in bone plate 108 to temporarily secure guide block 146 to bone plate 108, as shown in FIG. 13. During this attachment, the holes in guide block 146 are aligned with holes in bone plate 108. This type of fixation can also be utilized in the previously discussed method. Handle portion 150 is removably attached to guide block for easier insertion of bone plate 108. Then bone plate 108 is inserted to its anatomical position against bone 110, which can be initially influenced by contours and anatomical features and landmarks of the surface of bone 110 to allow the surgeon to find an appropriate fit of the surface of bone plate 108 against the corresponding surface of bone 110. This can be done by manipulating handle portion 150 to place bone plate 108 on a lateral surface of femur 110, for example. During insertion, the strut's twisted configuration can guide the implant anteriorly, if necessary, through the incision and along the length of femur 110. Both the distal and proximal fit of bone plate 108 should be confirmed, for example using fluoroscopy. In some cases, a proximal incision can be used to ensure correct fit of bone plate 108 against the proximal shaft of femur 110. If bone plate 108 is located in the desired position and is aligned distally and proximal with the femur 110, a pre fixation with k-wires both distally and proximally can be carried out.

Figure 14:
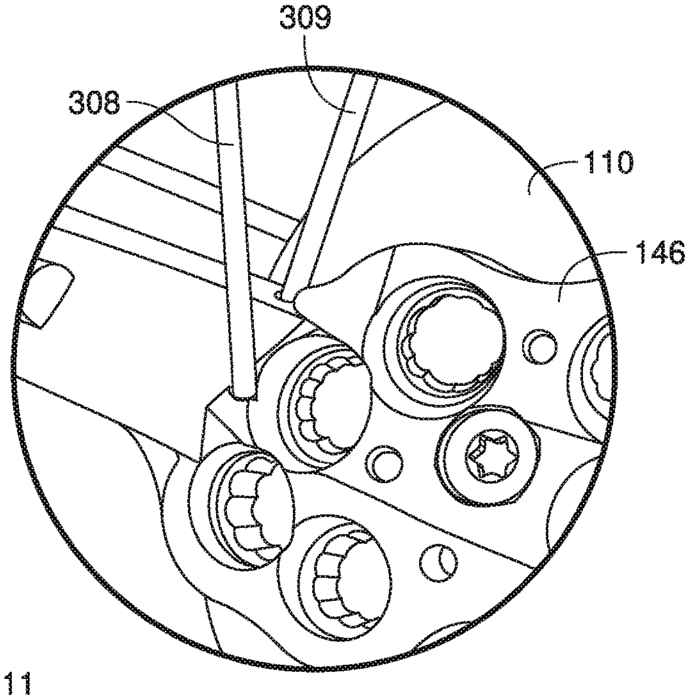
FIG. 14 is a perspective view of two k-wires connected with an insertion instrument to facilitate alignment.

With bone plate 108 placed against a lateral surface of femur 110, two additional k-wires 308, 309 are inserted in the area of the first hole of bone plate 108, the first hole being designed for interlinking with the nail. This corresponds to two k-wire holes in guide block 146, as shown in FIG. 14. The holes in guide block 146 do not necessarily pass through corresponding k-wire holes in bone plate 108. In fact, since k-wires 308, 309 are primarily used for confirming alignment, they need not be inserted in bone plate 108 or the underlying bone. Connecting k-wires 308, 309 can be done by inserting an end of each k-wire 308, 309 into dedicated holes of guide plate 146 such that the k-wires extend anteriorly from guide plate 146. As shown in FIG. 14, the holes for k-wires 308, 309 confine their projections to specific axes defined by the holes. Thus, when k-wires 308, 309 are inserted, they project away from guide plate 146 in a predefined manner set by the configuration and angle of the k-wire holes. Those projected axes are non-parallel as shown, such that k-wires 308, 309 are inserted in a non-parallel manner and extending along diverging axes. The k-wire holes themselves, and therefore the inserted k-wires 308, 309, are at a location on guide block 146 at a distal end of bone plate 108. In one embodiment, the inserted k-wires 308, 309 are disposed within a plane that is substantially parallel to the transverse plane when bone plate 108 is disposed against the surface of femur 110.

Aligning the specifically-positioned k-wires 308, 309, which are disposed at a distal end of bone plate 108, in a medial-lateral fluoroscopic view will indicate the recommended nail depth to ensure later interlinking of bone plate 108 and nail 303. This alignment is achieved when k-wires 308, 309 are overlapped so that one blends in or disappears behind the other in the medial-lateral fluoroscopic view, which is the medial-lateral direction located by a user for comparison with k-wires 308, 309. Locating this medial-lateral direction can be done by aligning the condyles of femur 110 under fluoroscopy. In that regard, the holes in guide block 146 are configured to orient each of k-wires 308, 309 so that they are parallel to the transverse plane of the bone when viewed in the medial-lateral direction.

Figure 16A:
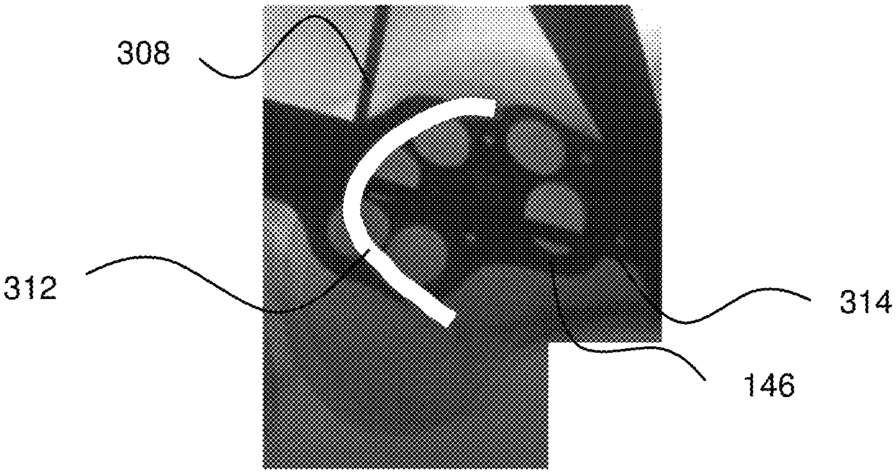
FIGS. 16A-C are medial-lateral views of possible implanted positions of a bone plate.
Figure 16B:
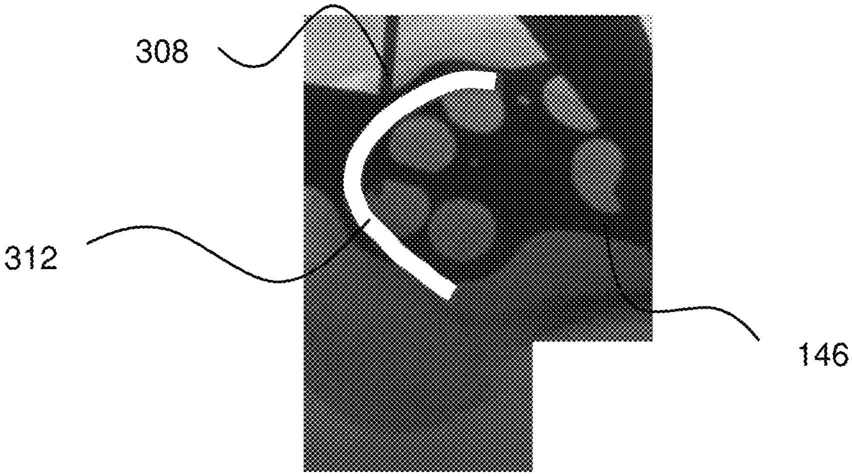
Figure 16C:
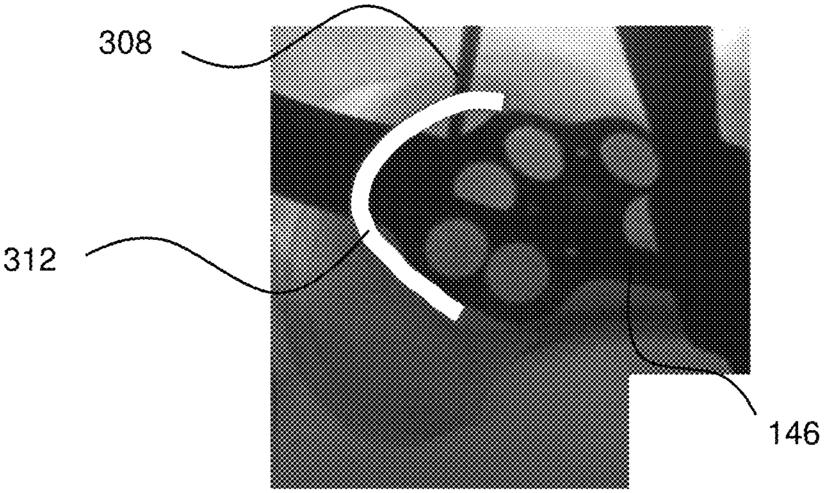

The entry point and position of k-wires 308, 309 in the medial-lateral view will help to indicate the relative depth and height of bone plate 108 relative to the axis along which nail 303 is to be inserted, such axis indicated by the k-wire or guide wire 314 initially inserted in the bone at the entry point of the bone. The entry point of k-wires 308, 309 can be viewed with respect to the distal end of the femoral condyles 116 in the medial-lateral fluoroscopic image. As shown in FIGS. 16A-C, aligning the overlapping k-wires 308, 309 with a surface of the intercondylar fossa (represented by line 312) of the femur will aid in confirming the proper positioning depth of bone plate 108 along a proximal-distal axis of the femur. Alignment of k-wires 308, 309 too close to the condylar surfaces, as shown in FIG. 16A, will indicate potential penetration of the knee joint by nail 303. Alignment of k-wires 308, 309 too far from the condylar surfaces, as shown in FIG. 16C, will indicate a deeper nail insertion that necessary to ensure linking of bone plate 108 and nail 303. Aligning k-wires 308, 309 in the medial-lateral view such that they substantially align with intercondylar fossa 312 provides a desired depth of the placement of bone plate 108 on femur 110, as shown in FIG. 16B. Furthermore, aligning bone plate 108 with the guide wire initially inserted in the bone at the entry point of the bone helps to confirm the relative height of bone plate 108 along an anterior-posterior axis of femur 108. This can be viewed for example in FIGS. 16A-C by considering the height of bone plate 108 with reference to guide wire 314. In one embodiment, the entry point of k-wire 308 in guide plate 146 is used to align along the axis of guide wire 314. In another embodiment, the entry point of k-wire 309 may be used for such alignment.

Figure 15:
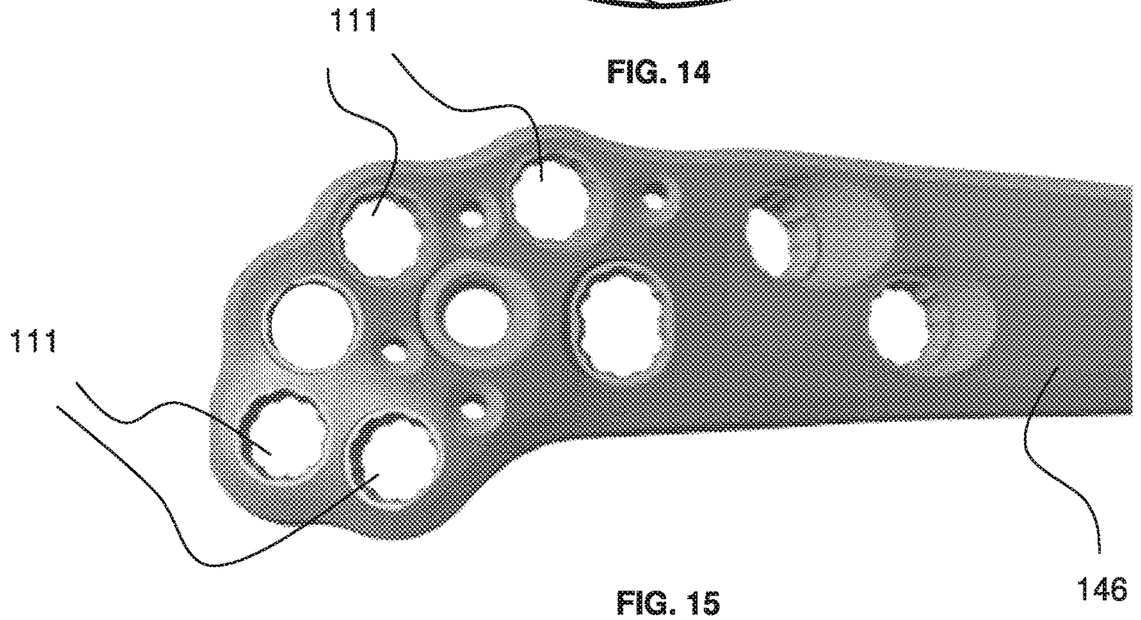
FIG. 15 is a perspective view of a bone plate according to one embodiment.

Once bone plate 108 is properly located against bone 110, it can optionally be pinned in place by k-wires, and a fixed angle sleeve and accompanying drill sleeve insert can be used to assist in inserting fixation screws through the bone plate and into the bone along trajectories that avoid the space in bone 110 in which nail 303 will reside. Thus, locking screws can be inserted through such holes in bone plate 108, which are identified as holes 111 in FIG. 15, such that two screws are anterior and two are posterior of the nail position. This can occur through the corresponding openings in guide block 146, or with guide block 146 detached.

After bone plate 108 is secured with screws 111 to the distal femur 110, all k-wires are removed. Nail 303 can then be inserted in a manner as described above in connection with the previous method, or in other conventional ways along the axis defined by guide wire 314. Targeting arm 301 and/or any cannula can then be aligned with the features of the implanted plate 108 and/or guide block 146 to properly position nail 303, as shown in FIG. 12. Thus, the initially implanted plate 108 permits guidance of nail 303 to its corresponding implanted position, by aligning the instrumentation used for inserting linking screws first with the plate holes to dictate the depth and rotation of nail 303. A linking fastener can then be inserted through both a hole of bone plate 108 and a hole in intramedullary nail 303. As described in the foregoing method, the relative position of bone plate 108 can not only be evaluated with respect to the bone for proper placement, but also with respect to the anticipated location of a subsequently inserted nail with assistance from guide wire 314.

While the foregoing methods have been described for a lateral plate 108, the same procedure can be carried out for a medial plate on the other side of bone 110.

Among the components described above, an implant alignment system or kit can be assembled that includes reference body 102 and alignment flange 104 rotatably and removably couplable thereto. Other variations of the system can include one or more of guide block 146, handle 106, and bone plate 108. The kit may also include alternative embodiments of each of the above-mentioned components, such as reference body 202, different size and shapes of bone plates, and the like. As such, a particular kit may be optimized for a particular fracture, such as a distal femur fracture. Any of the aforementioned kits can omit the reference body 102 and reference flange, for example including only one or more of guide block 146, one or more handles 106, and one or more bone plates 108. An operator may then select a kit corresponding to distal femur fractures and then select particular components within said kit to fix such a fracture.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A method of attaching a fixation construct to a long bone comprising:

attaching a guide block to a bone plate;

placing the bone plate against a surface of the long bone;

connecting two k-wires to the guide block;

locating the medial-lateral direction;

confirming an overlapping alignment of the two k-wires in the medial-lateral direction, the overlapping alignment defined by one of the k-wires being substantially hidden behind the other of the k-wires;

confirming a positioning of the bone plate with respect to the bone; and securing the bone plate to the bone.

2. The method of claim 1, wherein:

the step of attaching includes aligning holes in the guide block with holes in the bone plate.

3. The method of claim 2, wherein:

the step of attaching further includes securing the guide block to the bone plate by inserting a fixation screw through one of the holes in the guide block and into one of the holes in the bone plate.

4. The method of claim 1, wherein:

the step of attaching includes removably securing a handle to the guide block.

5. The method of claim 4, wherein:

the step of placing the bone plate includes manipulating the handle to place the bone plate on a lateral surface of the long bone.

6. The method of claim 1, wherein:

the step of placing the bone plate is initially influenced by contours of the surface of the long bone.

7. The method of claim 1, wherein:

the step of connecting the two k-wires includes inserting an end of each of the k-wires into the guide plate such that the k-wires extend anteriorly from the guide plate.

8. The method of claim 7, wherein:

the step of connecting the two k-wires further includes the k-wires being non-parallel.

9. The method of claim 7, wherein:

the step of connecting the two k-wires includes the k-wires extending along diverging axes.

10. The method of claim 7, wherein:

the step of connecting the two k-wires includes the k-wires being disposed within a plane that is substantially parallel to the transverse plane.

11. The method of claim 7, wherein:

the step of connecting the two k-wires includes inserting the ends of each of the k-wires at a location on the guide block at a distal end of the bone plate placed against the surface of the long bone.

12. The method of claim 1, wherein:

the step of securing the bone plate includes inserting a fastener through a hole of the bone plate and into the long bone.

13. A method of attaching a fixation construct to a long bone comprising attaching a guide block to a bone plate;

placing the bone plate against a surface of the long bone;

connecting two k-wires to the guide block;

locating the medial-lateral direction including aligning condyles of the long bone under fluoroscopy;

confirming an overlapping alignment of the two k-wires in the medial-lateral direction;

confirming a positioning of the bone plate with respect to the bone; and securing the bone plate to the bone.

14. The method of claim 13, wherein:

the step of confirming the positioning of the bone plate with respect to the bone includes aligning the overlapping k-wires with a surface of the intercondylar fossa of the femur to confirm the positioning of the bone plate along a proximal-distal axis of the femur.

15. The method of claim 13, further comprising inserting a guide wire at an entry point of the distal end of the long bone and into the long bone parallel to a medullary canal thereof, wherein the step of confirming the positioning of the bone plate with respect to the bone includes aligning the bone plate with the guide wire to confirm the positioning of the bone plate along an anterior-posterior axis of the femur.

16. A method of attaching a fixation construct to a long bone comprising:

attaching a guide block to a bone plate;

placing the bone plate against a surface of the long bone;

connecting two k-wires to the guide block;

locating the medial-lateral direction;

confirming an overlapping alignment of the two k-wires in the medial-lateral direction;

confirming a positioning of the bone plate with respect to the bone;

securing the bone plate to the bone; and inserting an intramedullary nail into the medullary canal of the long bone.

17. The method of claim 16, wherein:

the step of inserting the intramedullary nail includes aligning a targeting arm attached to a proximal end of the nail with a portion of the secured bone plate.

18. The method of claim 17, further comprising:

inserting a fastener through both a hole of the bone plate and a hole in the intramedullary nail.

19. The method of claim 16, wherein:

the step of inserting the intramedullary nail includes inserting the intramedullary nail such that a hole axis of the bone plate aligns with a hole axis of the intramedullary nail.

* * * * *